United States Patent [19]

Bonnard

[11] Patent Number: 4,925,315
[45] Date of Patent: May 15, 1990

[54] CALORIMETRIC APPARATUS

[76] Inventor: John A. Bonnard, P O Box 781393, Sandton, 2146, South Africa

[21] Appl. No.: 213,674

[22] Filed: Jun. 30, 1988

[30] Foreign Application Priority Data

Jul. 2, 1987 [ZA] South Africa .................. 87/4788

[51] Int. Cl.$^5$ .................. G01K 17/06; G01N 25/44
[52] U.S. Cl. .................. 374/31; 165/32; 422/51
[58] Field of Search .................. 374/31, 33, 34, 38, 374/36; 422/91, 57; 436/123, 122

[56] References Cited

U.S. PATENT DOCUMENTS

| 550,943 | 12/1895 | Carpenter | 374/28 |
| 4,616,938 | 10/1986 | Bonnard | 374/38 |

FOREIGN PATENT DOCUMENTS

| 0113359 | 7/1982 | Japan | 374/32 |
| 0571218 | 10/1973 | Switzerland | 374/33 |
| 0830354 | 5/1981 | U.S.S.R. | 374/33 |

OTHER PUBLICATIONS

Automatically Controlled Isothermal-Adiabatic Colorimeter, L. A. Hiller, Jr. et al., Review of Scientific Instruments, 3/1962, vol. 33, No. 3, pp. 323-330, 374/33.

Primary Examiner—Daniel M. Yasich
Attorney, Agent, or Firm—Young & Thompson

[57] ABSTRACT

Colorimetric apparatus which includes a water tank, a container in the tank, a pressure vessel in the container, and a pump. The apparatus is worked in three phases. In the first phase the water in the tank is mixed and brought to a desired temperature. In the second phase water is pumped from the tank, through a jacket which surrounds the pressure vessel, and back to the tank, to bring the pressure vessel to the tank temperature. After a sample of material is combusted in an oxygen atmosphere in the pressure vessel, the third phase takes place. Water is circulated in a closed path which includes the jacket and the temperature of this water is monitored. The variation of this temperature is used to calculate the colorific value of the substance.

5 Claims, 2 Drawing Sheets 4,925,315

CALORIMETRIC APPARATUS

BACKGROUND OF THE INVENTION

This invention relates generally to the determination of the calorific value of a substance. More particularly the invention is concerned with calorimetric apparatus which is compact and easy to operate.

SUMMARY OF THE INVENTION

The invention provides calorimetric apparatus which includes a tank which in use receives a liquid, a container which is located at least partly within the tank, the container being surrounded at least partly by liquid in the tank, a pressure vessel which is located in the container, the pressure vessel in use receiving a substance which is combusted so that its calorific value can be determined, pump means for passing liquid from the tank through a jacket which is in thermal contact with the pressure vessel, and back to the tank, thereby to stabilise the temperature of the pressure vessel at the temperature of the liquid in the tank, before combustion of the substance, means for circulating liquid in a closed path, which includes the jacket, after combustion of the sample, and temperature sensing means for monitoring the temperature variation of the liquid flowing through the jacket at least after combustion of the sample.

The apparatus may include a receptacle which is at least partly immersed in the liquid in the tank, the pump means being located in the receptacle. Alternatively, the pump means may be located in the container in which the pressure vessel is located.

The apparatus may include heat exchanger means which is located inside the pressure vessel, and conduit means which is connected in the closed path and which is in thermal contact with the heat exchanger means.

The substance which is combusted may be located in a crucible which is mounted in the pressure vessel. Preferably the conduit means supports the crucible and the heat exchanger means.

The temperature sensing means may be located in a body of the pump means. The temperature sensing means may be used to monitor the temperature of liquid which passes through the pump means.

The invention also extends to a method of determining the calorific value of a substance which includes the steps of placing a sample of the substance of a predetermined mass in a crucible in a pressure vessel, sealing the pressure vessel, locating the pressure vessel in a container which is at least partly immersed in liquid in a tank, passing liquid from the tank through a jacket which is in thermal contact with the pressure vessel thereby to stabilise the temperature of the pressure vessel at the temperature of the liquid in the tank, charging the interior of the pressure vessel with an oxygen-rich gas, causing combustion of the sample within the pressure vessel, circulating liquid in a closed path which includes the jacket, and monitoring the variation in temperature of the liquid in the closed path attributable to the combination of the sample.

The closed path may include a portion which extends into the pressure vessel.

BRIEF DESCRIPTION OF THE DRAWINGS

The invention is further described by way of example with reference to the accompanying drawings in which.

DESCRIPTION OF PREFERRED EMBODIMENT

Figure 1:
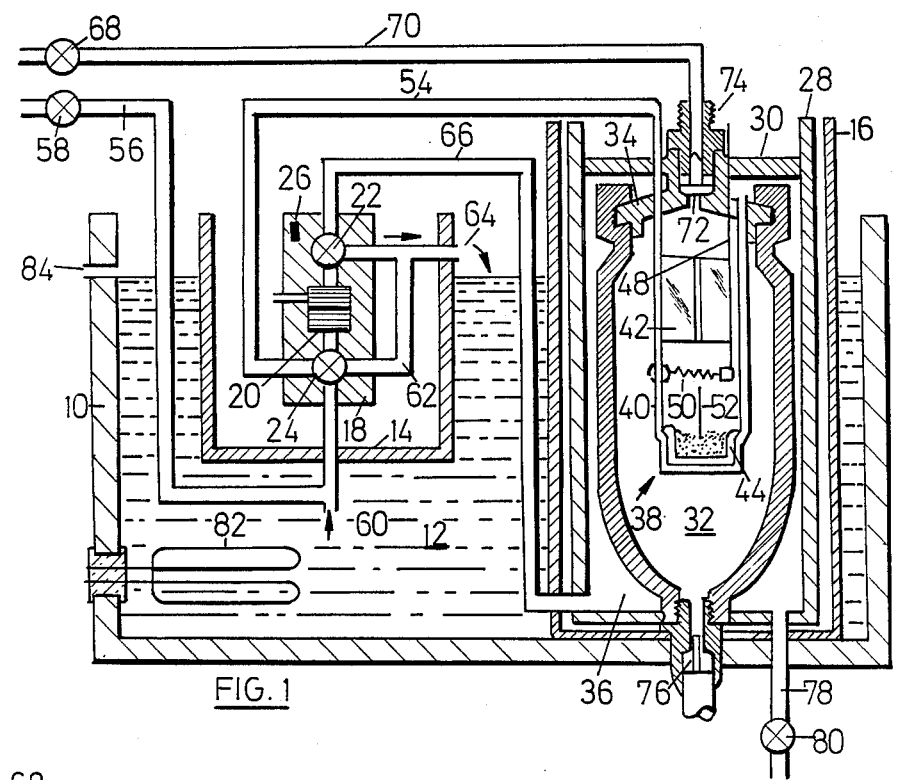
FIG. 1 is a sectioned side view of apparatus according to the invention in a stand-by mode.

The accompanying drawings illustrate a tank 10 which holds water 12. Located in the tank are a receptacle 14 and a container 16.

The receptacle 14 houses a pump body 18 in which is located a gear pump 20 which is driven by means of a motor, not shown, two pneumatically operated valves 22 and 24 respectively, and a temperature sensor 26. Connections made to the valves for their operation and to the sensor for recording its readings are not shown for the sake of clarity.

The container 16 has located in it a housing 28 which has a lid 30. A pressure vessel 32 with a bayonet locking cap 34 is locatable in the housing 28. A water jacket 36 is defined by the volume between the housing 28 and the exterior of the pressure vessel 32.

Located in the pressure vessel 32 is a crucible mounting arrangement 38. This arrangement includes a conduit 40 which is bent roughly into a U-shape and which includes cruciform heat exchanger fins 42 secured to the upright limbs of the conduit. A crucible 44 is engageable with formations 46 at the lower end of the conduits.

An electrode 48, see for example FIG. 1, extends through the bayonet cap 34 to a firing wire 50 anchored to one of the limbs of the conduit 40.

In use of the apparatus cotton 52 attached to the firing wire hangs downwardly into a sample of material which is to be combusted and which is located in the crucible 44.

Figure 2:
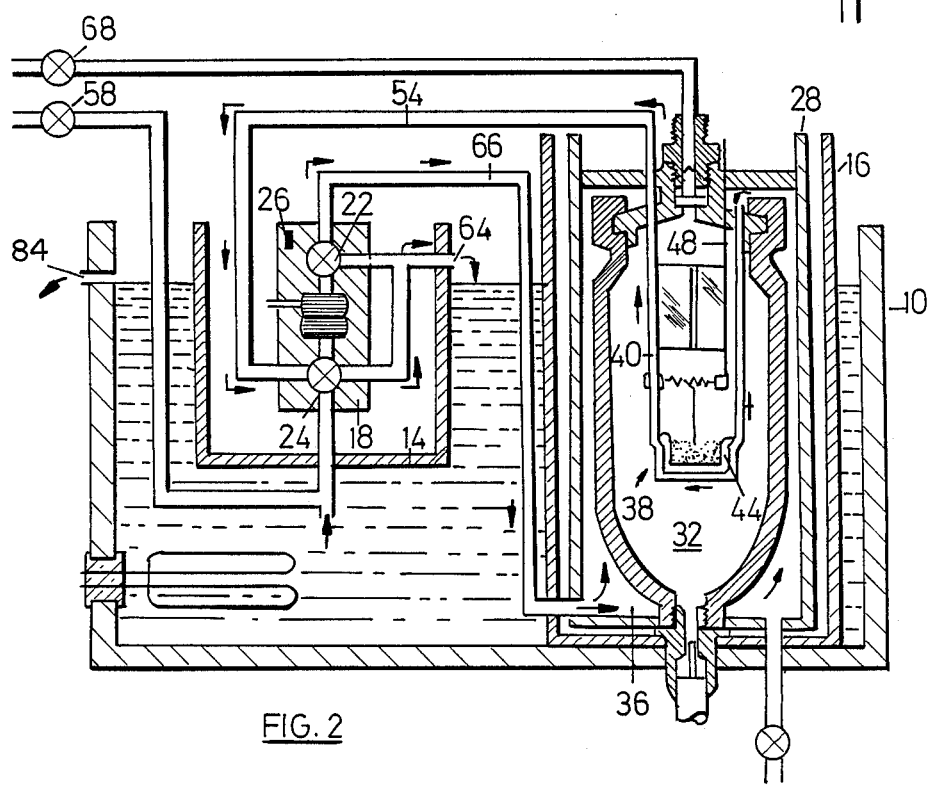
FIG. 2 is a view similar to that of FIG. 1 of the apparatus in a stabilise mode.
Figure 3:
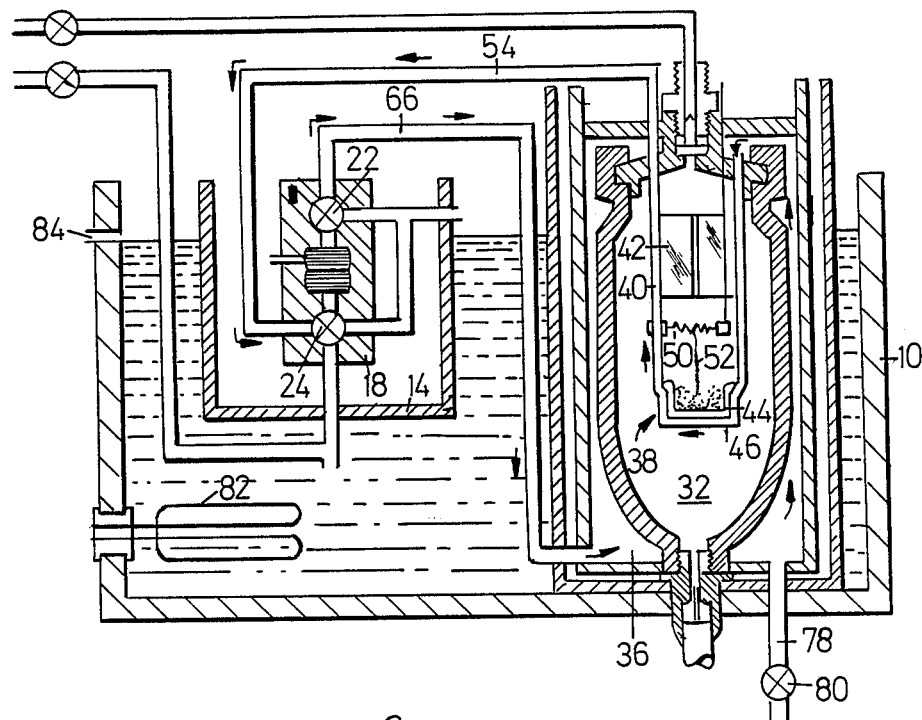
FIG. 3 is a view similar to FIG. 1 of the apparatus in an analyse mode.
Figure 4:
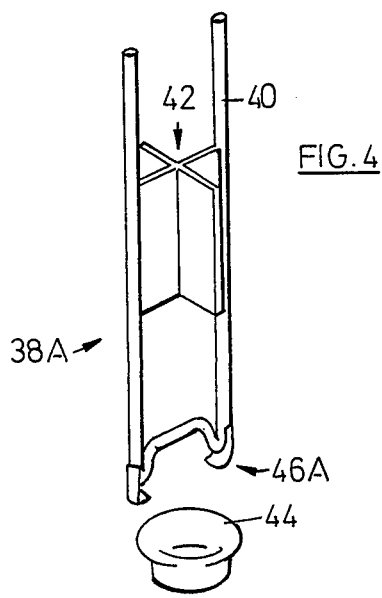
FIG. 4 is a perspective illustration of a crucible mounting arrangement used in the apparatus of FIGS. 1 to 3.

The arrangement 38 of FIGS. 1 to 3 can be substituted by the arrangement 38A shown in FIG. 4, which is substantially similar to the arrangement 38 but which has differently shaped formations 46A which engage with the crucible 44.

A pipe 54 extends from the valve 24 in the pump body and is connected to the conduit 40 in the pressure vessel. The other side of the conduit 40 terminates in the jacket 36. A pipe 56 which has a valve 58 connected to it is connected to a cold water source. This pipe is used to admit water into the tank 10 and is connected to the valve 24. The valve 24 is a four-port change-over valve. The pipe 56 has a port 60 into the water in the tank.

A pipe 62 connects one port on the valve 24 to a port on the valve 22 and has an outlet 64 which discharges into the tank.

A pipe 66 from one port of the valve 22 is directed into the jacket 36.

A source of oxygen, not shown, is connected via a valve 68 to a pipe 70 which via a one-way valve 72 in a connecting nozzle 74 at the upper end of the pressure vessel 32 and of the housing 28 terminates in the interior of the pressure vessel.

A release valve 76 is located at the lower end of the pressure vessel. A drain pipe 78 in series with a drain valve 80 is connected to the water jacket 36.

An electrical heater 82 is positioned in the tank. The heater is under the control of apparatus, not shown, which in turn is responsive to the temperature sensor 26. The electrical control circuitry is not shown for it is substantially conventional in construction and operation.

As has been pointed out FIGS. 1 to 3 respectively illustrate the apparatus of the invention in a stand-by mode, a stabilise mode, and in an analyse mode.

In use of the apparatus a weighed amount of a sample to be analysed is placed in the crucible 44 which is positioned in the crucible holder 38. The cotton 52 is placed over the firing wire 50, with one end of the cotton contacting the sample in the crucible.

The bayonet locking cap 34 is lowered onto the body of the pressure vessel 32 which, it is to be pointed out, is permanently in the housing 28. The bayonet cap is fixed to the lid 30 and as the cap is twist-locked into position and the lid 30 is simultaneously secured to the housing.

It is pointed out that the connections of the pipes to the housing and the pressure vessel are shown somewhat schematically in that it is apparent from the aforegoing that the lid 30 and the cap 34 are detachable from the housing and the pressure vessel respectively. The pipes which extend through to these components are adapted to accommodate this movement. Either the pipes are flexible or, alternatively, quick release connections are provided for the pipes.

In the stand-by mode water of FIG. 1 is circulated from the port 60 and through the valves 24 and 22, exiting from the outlet 64. This process mixes the water in the tank while it is being heated by the heater 82 to a required fixed temperature. The sensor 26 which is mounted in the pump body 18 is sued to monitor the tank water temperature in order for the heater element action to be electronically controlled.

In the stabilise mode shown in FIG. 2 the pressure vessel is brought to a require stable temperature state. Water is pumped from the tank through the valves 24 and 22, along the pipe 66 and into the jacket 36 around the pressure vessel. The water flows from the jacket through the conduits 40 which form the crucible support and exits via the pipe 54. The water flow from the pipe 54 traverses the cross-over valve 24 and emerges from the outlet 64.

As has been pointed out in the stabilise mode the pressure vessel and the housing are brought to the tank temperature. During this mode the temperature of the water in the system as a whole is monitored, using a signal generated by the temperature sensor 26, and can be adjusted, if required, either by action of the electrical heater 82 or by the addition of cold water which is admitted by opening the valve 58. The tank 10 has an overflow 84 which fixes the maximum level of the water in the tank.

At the commencement of the stabilise mode the release valve 76 at the bottom of the vessel is closed and the vessel is pressurised, by opening the valve 68, with oxygen.

After the stabilise mode, the analyse mode is initiated. The temperature of the water circulating through the jacket 36 is read and stored. The sample in the crucible is ignited by passing an electric current from a source, not shown, through the electrode 48 and to the firing wire 50. The cotton 52 is ignited and in turn ignites the sample. The firing wire 50 is itself not burnt and can be used for a number of calorific determinations.

The combustion of the sample results in the release of a quantity of heat which is related to the calorific value of the sample. This raises the temperature of water which is circulated by the pump 20 along a closed path which extends through the valves 24 and 22, along the pipe 66, upwardly through the jacket 36, through the conduit 40 and along the pipe 54 back to the valve 24.

The heat exchanger fins 42 effectively assist in transferring heat to the circulating water in the conduit 40.

The temperature of the water in the closed path is constantly monitored. The temperature increases until it reaches a maximum peak. This peak is stored and, together with the initial temperature, is used to determine the calorific value of the sample. The isothermal calculation method is used, basing the "final slope" of predetermined data that is stored, in a suitable memory. The slope is related to the temperature increase that took place approximately as per the American Bureau of Mines Cooling Correction ASTMD $3286 \times 2.2.3$.

Once all pertinent data relating to the combustion of the sample has been recorded the pressure vessel is depressurised by opening the release valve 76. Residues in the vessel may be rinsed from the vessel. The drain valve 80 is opened and the hot water is drained from the jacket.

The next sample is loaded into the crucible and the process is repeated. Cold water enters the system via the valve 58 to replace the water drained away at the end of the previous analysis. This cold water passes through the pressure vessel first and so assists in cooling the vessel to ready it for the following cycle.

The apparatus of the invention is compact and enables the calorific value of the substance to be determined efficiently and rapidly. The heat exchanger located in the pressure vessel, and the fact that water is passed into the pressure vessel itself, assists in a rapid determination of calorific value.

I claim:

1. Calorimetric apparatus comprising a tank which in use receives a liquid, a container which is located at least partly within the tank, the container being surrounded at least partly by liquid in the tank, a pressure vessel which is located in the container, the pressure vessel including a crucible which in use receives a sample of a substance which is combusted so that its calorific value can be determined, a pump for passing liquid from the tank into a volume which is in thermal contact with the pressure vessel, and back to the tank, thereby to stabilize the temperature of the pressure vessel at the temperature of the liquid in the tank, before combustion of the substance, a heat exchanger which is located inside the pressure vessel, a conduit which is in thermal contact with the heat exchanger, means for circulating liquid through the conduit after combustion of the sample, and a temperature sensor for monitoring the change in the temperature of the liquid circulating through the conduit due to combustion of the sample.

2. Calorimetric apparatus according to claim 1 which includes a receptacle which is at least partly immersed in the liquid in the tank, the pump means being located in the receptacle.

3. Calorimetric apparatus according to claim 1, wherein the conduit supports the crucible and the heat exchanger.

4. Calorimetric apparatus according to claim 1, wherein the temperature sensor is located in the pump and monitors the temperature of the liquid which passes through the pump.

5. Calorimetric apparatus according to claim 1, wherein the conduit is at least partially disposed within the pressure vessel.

* * * * *